United States Patent [19]

Lazarus

[11] Patent Number: 5,209,735
[45] Date of Patent: May 11, 1993

[54] EXTERNAL GUIDE WIRE AND ENLARGEMENT MEANS

[76] Inventor: Harrison M. Lazarus, 324 10th Ave., Ste. #260, Salt Lake City, Utah 84103

[21] Appl. No.: 750,210

[22] Filed: Aug. 27, 1991

Related U.S. Application Data

[63] Continuation-in-part of Ser. No. 610,349, Nov. 2, 1990, abandoned, which is a continuation of Ser. No. 448,977, Dec. 12, 1989, abandoned, which is a continuation of Ser. No. 270,661, Nov. 7, 1988, Pat. No. 4,886,500.

[51] Int. Cl.⁵ .............................................. A61M 5/00
[52] U.S. Cl. .................................... 604/164; 128/657; 128/772
[58] Field of Search ............... 604/158, 164, 178, 280, 604/264; 128/656–658, 772

[56] References Cited

U.S. PATENT DOCUMENTS

3,731,671  5/1973  Mageoh ................................. 604/95
4,534,363  8/1985  Gold .
4,545,390  10/1985  Leary .
4,553,960  11/1985  Lazarus et al. ..................... 604/158
4,830,023  5/1989  De Toledo et al. ................. 128/772
4,886,500  12/1989  Lazarus ............................... 604/164

Primary Examiner—Stephen C. Pellegrino
Assistant Examiner—Michael Rafa
Attorney, Agent, or Firm—Trask, Britt & Rossa

[57] ABSTRACT

Structure for facilitating the insertion and placement of medical apparatus into the body of a patient is disclosed which comprises a guide wire having a lumen sized to adapt about the elongated structure of needle-like means. In use, the distal end of the guide wire is placed about the needle-like means and the tip of the needle-like means is inserted through the tissue of the patient. Once inserted, the needle-like means is disassociated from the guide wire and the guide wire is advanced into the patient's body. The guide wire may have enlargement means associated therewith for enlarging or dilating the opening formed in the tissue of the patient by insertion of the needle-like means. A kit including the needle-like means and guide wire is also disclosed.

19 Claims, 7 Drawing Sheets

EXTERNAL GUIDE WIRE AND ENLARGEMENT MEANS

BACKGROUND OF THE INVENTION

1. Related Applications

This application is a continuation-in-part of Ser. No. 610,349 filed Nov. 2, 1990 ABN, is a continuation of Ser. No. 448,977, filed Dec. 12, 1989 and now abandoned, which is a continuation of Ser. No. 270,661 filed Nov. 7, 1988 now issued as U.S. Pat. No. 4,886,500.

2. Field

This invention relates to medical apparatus, and more particularly to guide wires which are insertable into a body to guide medical apparatus, such as cannulas, to a desired position within the body, and to kits therefor.

3. State of the Art

Today many different kinds of medical apparatus are inserted into patients for administering a wide variety of therapies. For example, a catheter of the type which is comprised of a trocar and a cannula may be inserted into a blood vessel to, for example, administer different fluids including whole blood, salt solution, and other therapeutic liquids through the cannula after removal of the trocar. The catheter may also be used to place instruments relative to the interior of a patient, or to remove blood. For example, U.S. Pat. No. 4,553,960 to Lazarus, et al., dated Nov. 19, 1985 illustrates and describes a peritoneal lavage procedure employing a catheter, a cannula and a guide wire all inserted into the peritoneal cavity.

It may be necessary or desirable in some medical procedures to position a cannula having a relatively large diameter into a body. Insertion and placement of a larger cannula into a body is often difficult and may even require the use of a scalpel to make a small incision for enlarging the opening. Therefore, the use of a guide wire to assist in directing the insertion and placement of a cannula may be beneficial for many of the cannula placement procedures, not only to facilitate placement but also to minimize the need for making an incision.

Typically, a small trocar having a cannula positioned thereover is used to penetrate the skin in order to position the cannula within, for example, a blood vessel. The trocar is then removed, and a guide wire is inserted into the cannula and positioned within the blood vessel. The cannula may then be removed from about the guide wire, and a larger diameter cannula may then be inserted over the guide wire and positioned into the blood vessel. The guide wire is thereafter removed.

In some instances, a hollow needle may be used without a cannula. That is, the hollow needle is inserted into the patient after which a guide wire is inserted through the hollow needle. Cannulas may then be inserted over the guide wire.

U.S. Pat. No. 4,533,960, referred to above, illustrates use of a guide wire in an exemplar medical procedure. U.S. Pat. No. 4,545,390 to Leary, dated Oct. 8, 1985, also describes use of a guide Wire. U.S. Pat. No. 4,534,363 to Gold, dated Aug. 13, 1985, discloses a special form of a guide wire.

Guide wires heretofore known are spring wound, and are similar in structure to piano wire. In some instances, they have varying diameters between a distal or interiorly positioned end and a proximal or exteriorly positioned end. Such wires are typically sized to be positioned through the interior of small cannulas in a fashion similar to that illustrated in U.S. Pat. No. 4,553,960 referenced hereinabove.

The procedures known to applicant for placement of a cannula require a number of different and consecutive steps. No guide wire has yet been suggested which, in use, would minimize the number of procedural steps associated with the positioning of medical apparatus in a body, or would minimize the steps associated with the cannulation of a patient when a guide wire is used. Thus, there remains a need in the medical field for a guide wire that can provide simplified means for conducting such procedures.

SUMMARY OF THE INVENTION

Structure for insertion into the tissue of a patient comprises needle-like structure having an elongated portion with a proximal end and a distal end defining piercing means, and a guide wire having a body with a distal end, a proximal end and a lumen sized and shaped for positioning slidably and snugly about the elongated portion of the needle-like structure. The body of the guide wire is sized in length to extend from interior a patient to exterior the patient.

In one embodiment, the body of the guide wire is a continuous length of material formed into a plurality of hairpin loops adjacently positioned. The hairpin loops are laterally curved to form the lumen which is positionable about the elongated portion of the needle-like structure. In an alternative embodiment, the body of the guide wire is a continuous length of material formed into a plurality of adjacent coils.

In some embodiments, the body of the guide wire includes a transition section between a first portion and a second portion of the body of the guide wire. The first portion is positionable about the elongated portion of the needle-like structure while the second portion of the body of the guide wire extends away from the needle-like structure. The first portion of the body positionable about the elongated portion of the needle-like structure may fair toward the exterior surface of the elongated portion to facilitate entry of the guide wire into the patient. By "fair" is meant that the exterior surface of the guide wire is shaped to diminish in dimension thereby tapering smoothly to conform with the exterior surface of the elongated portion of the needle-like structure.

In another embodiment, the body of the guide wire includes a tube positioned proximate the distal end of the body. The tube has an opening therein and a bore sized and shaped to receive the elongated portion of the needle-like structure therethrough. When the elongated structure of the needle-like structure is inserted through the opening and into the bore, the piercing means of the needle-like structure extends beyond the distal end of the body providing means for piercing the tissue of the patient.

The needle-like structure used with the guide wire generally includes an elongated portion extending from a hub. The elongated portion has a distal end defining a sharp tip for facilitating penetration through the tissue of a patient. The elongated portion may be a hollow needle of the type typically used in association with a syringe for delivering fluid therethrough, or may be a solid rod of material, such as a stylus. A particularly suitable needle-like structure for use with the guide wire is a trocar.

The elongated portion of the needle-like structure may, in one embodiment, include a recessed portion which extends from proximate the distal end to proximate the proximal end of the elongated portion of the needle-like structure. The recessed portion has a smaller cross section relative to the cross section of the elongated portion. The recessed portion provides a section of the elongated portion around which the first portion of the guide wire body may be positionable so that the exterior surface of the guide wire is substantially flush with the exterior surface of the non-recessed portion of the elongated portion.

The second portion of the body of the guide wire may be a continuous coil or series of hairpin loops. Alternatively, the second portion of the body may be a substantially straight length of material which extends from the first portion positioned about the elongated portion of the needle-like structure.

The guide wire may provide means for enlarging the point of entry of the guide wire into a patient. Such means may take the form of a dilator associated with the guide wire which is slidably disposed thereover. Alternatively, such means may take the form of dilating structures associated with the guide wire which, as the guide wire is advanced into the patient, provide increasing dilation of the point of entry of the guide wire into the patient.

A kit containing the structure for insertion of a guide wire into the tissue of a patient is provided. The kit may contain a needle-like structure, a guide wire, and related supplies and equipment, such as cannulae, swabs and disinfectant, for inserting the guide wire into a patient. The components of the kit are retained in a suitable package for maintaining the components together and in a sterile condition prior to use.

BRIEF DESCRIPTION OF THE DRAWINGS

In the drawings, which illustrate the best mode presently contemplated for carrying out the invention.

DETAILED DESCRIPTION OF THE ILLUSTRATED EMBODIMENTS

A guide wire is provided for use with a needle-like device for insertion into a patient. The guide wire may further provide means for enlarging the point of entry of the guide wire into a patient in preparation for the insertion of other devices useful for performing medical therapy. The guide wire is generally sized to be insertable into a desired cavity or vessel of a patient, and may be particularly sized to be insertable within a very small blood vessel. The guide wire has length sufficient to provide a portion positionable in the interior of the patient while another portion is positioned exterior to the patient.

Figure 1:
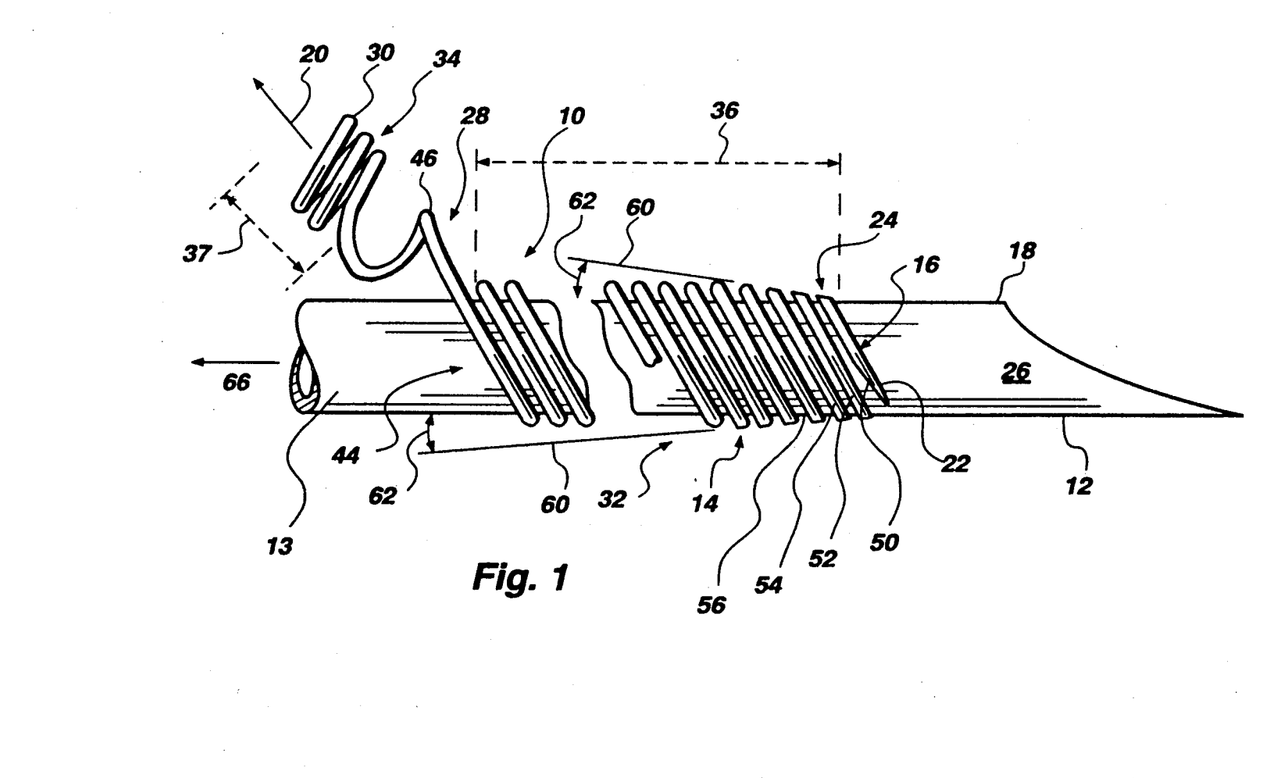
FIG. 1 is an enlarged side view of a guide wire of the invention in position for placement.

Referring to FIG. 1, a guide wire of the invention is generally referred to by the numeral 10 and is here shown positioned about a needle-like structure or trocar 12 which is similar in structure to a trocar typically associated with a catheter. The term catheter as used herein refers to the associative structure of a trocar and a cannula in which the trocar is slidably and snugly positionable through the interior of the cannula which is typically a tube. The trocar 12 includes an elongated portion 13 having a sharp tip 18 formed at a distal end and a hub 38 (shown in FIG. 2) formed at a proximal end of the elongated portion 13. The needle-like structure used with the guide wire may be of any type which provides an elongated portion having a tip formed at one end, and preferably a hub formed at the other end.

The guide wire, as shown by FIG. 1, includes a body 14 having a lumen 16 which is sized and shaped to receive the elongated portion 13 of the trocar 12 and to slidably and snugly adapt thereabout. The body 14 extends from proximate the tip 18 of the trocar 12 to exterior the body of the patient, as suggested by arrow 20. The tip 22 of the guide wire 10 at the distal end 24 thereof may be formed to fair toward the exterior surface 26 of the trocar 12. By "fair" is meant that the guide wire 10 is shaped to diminish in dimension and taper smoothly to conform with the exterior surface 26 of the trocar 12.

The body 14 of the guide wire 10 includes a transition section 28 intermediate the distal end 24 of the body 14 and the proximal end 30 of the body 14, and provides a point of differentiation between a first portion 32 and a second portion 34 of the body. The first portion 32 is sized in length 36 to extend from proximate the tip 18 of the trocar 12 to proximate the hub 38 (shown in FIG. 2). Thus, the first portion may be from about 4.0 centimeters to about 26.0 centimeters in length. The second portion 34 is sized in length 37 to extend from proximate the hub 38 (shown in FIG. 2) to exterior the patient's body. The length 37 of the second portion 34 may vary, but the length is typically an amount sufficient to allow insertion of the guide wire 10 associated with the trocar 12 and to allow a cannula (not shown) to be placed over the guide wire 10 for insertion into the patient's body, with an additional amount to allow manipulation of the guide wire 10 by the user. Thus, the guide wire 10, in overall length, may be from about 30 centimeters to about 65 centimeters, but other lengths may be suitable based on the desired or necessary application.

The transition section 28 is an area of the body 14 of the guide wire 10 which provides a point of division between the first portion 32 and the second portion 34 so that an access 44 is formed for insertion of the elongated portion 13 of the trocar 12 into the lumen 16 of the first portion 32. The lumen 16 of the first portion 32 is sized to receive a trocar 12, and may be sized to accommodate from about a 27-gauge trocar to about a 13-gauge trocar or larger. In FIG. 1, the guide wire 10 is shown as a continuous coil 46 and the transition section 28 is an elastically deformable portion of the continuous coil 46. The transition section 28, however, may be inelastically deformable where required by the procedure.

Figure 2:
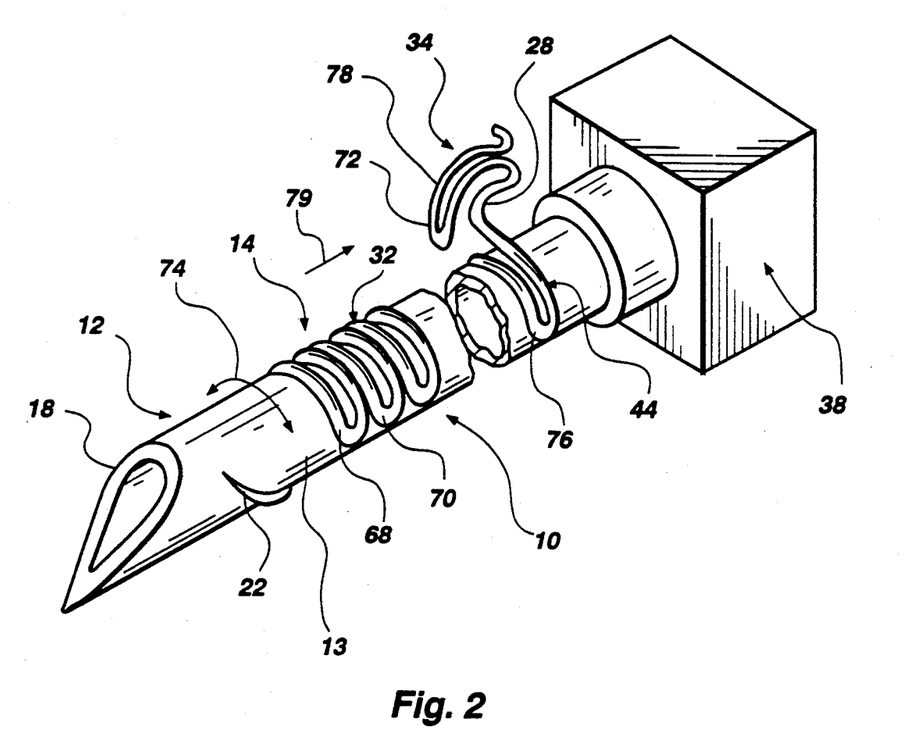
FIG. 2 is an enlarged perspective view of a guide wire of the invention illustrating a looped configuration.

The distal end 24 of the first portion 32 of the guide wire 10 is angled to taper toward the exterior surface 6' of the trocar 12. That is, the coils 50, 52, 54, and 56 at the distal end 24 of the guide wire 10 have decreased diameters so that the coils 50, 52, 54, and 56 angle smoothly into the exterior surface 26 of the trocar 12. The tip 22 of the guide wire is conically shaped. Thus, the distal end 24 of the guide wire forms a smooth surface 60 with the tip 18 of the trocar 12 as it angles away from the tip 18. The angle 62 is selected to reduce resistance of the guide wire 10 as the trocar 12 is urged through the skin of a patient. The angle 62 may be from about four degrees to about twenty degrees. When the trocar 12 is urged into a patient's skin, the first portion 32 of the guide wire 10 tends to move in a rearward direction 66 away from the tip 8 of the trocar 12 and toward the hub 38, as illustrated in FIG. 2. The hub 38 limits the rearward movement 66 of the first portion 32 of the guide wire 10 under conditions of insertion.

FIG. 2 illustrates an alternative form of the guide wire 10 in which the body 14 is formed of a plurality of loops 68, 70 which are joined together in side-by-side arrangement. The guide wire 10 of this embodiment is formed from a continuous piece of wire 72 which is bent into hairpin loops. The loops 68, 70 substantially encircle the circumference 74 of the trocar 12 but do not completely surround the trocar 12. The transition section 28 forms a point of differentiation between the first portion 32 and the second portion 34 of the body 14 of the guide wire 10, and forms an access 44 through which the trocar 12 may be inserted into the first portion 32 of the body 14. The transition section 28 is formed by an elastic deformation of adjacent loops 76 and 78; however, an inelastic deformation may be suitable. The tip 22 of the guide wire is conically shaped to taper smoothly into the exterior surface 26 of the trocar 12.

Referring to FIGS. 1 and 2, in use, the trocar 12 is inserted through access 44 in the first portion 32 of the guide wire 10. The tip 18 of the trocar 12 is positioned at the desired point of penetration of a patient's tissue, and the trocar 12 is then inserted into the tissue. As the trocar 12 enters into the tissue, the first portion 32 of the body 14 of the guide wire 10 is forced rearwardly in direction 79 toward the hub 38. Once the trocar 12 and first portion 32 of the guide wire are positioned within the patient's body, the trocar 12 may be removed, via access 44, from the first portion 32 of the guide wire 10.

Figure 3:
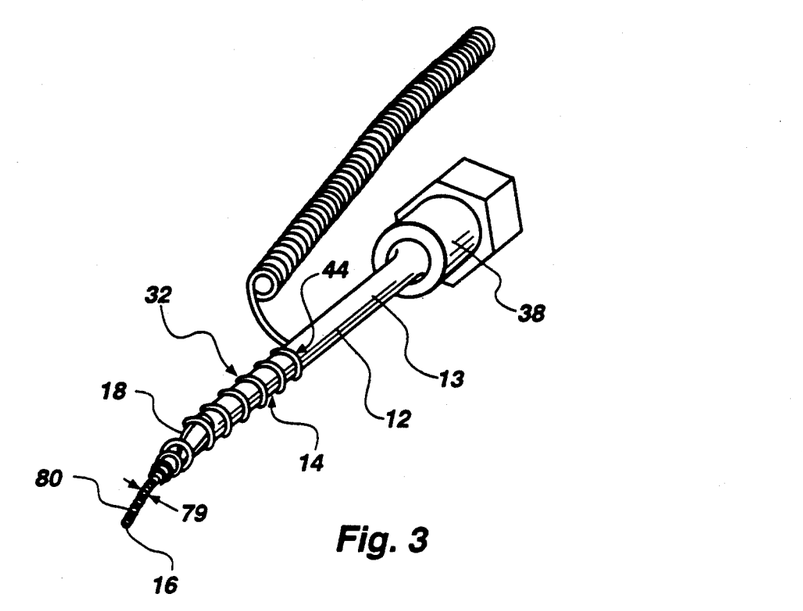
FIG. 3 is a perspective view of a guide wire partially positioned about a trocar.

When the guide wire 10 is being placed into a very small space, such as a small blood vessel for example, it may prove difficult to insert the guide wire 10 into the vessel past the initial point of penetration of the vessel. Thus, it may be particularly desirable to form the guide wire from a highly elastic material which, as illustrated in FIG. 3, provides considerable reduction of the lumen 16 of the body 14 of the guide wire 10 once the trocar 12 is removed, via access 44, from the first portion 32. A particularly suitable material for use in the guide wire 10 illustrated in FIG. 3 is nitinol, an alloy of nickel and titanium which may be deformed from an original shape to which it will return upon application of heat or cold. The distal portion 80 of the guide wire 10, therefore, maintains a very small diameter 79 and is more easily inserted into a small space within the patient's body.

Figure 3A:
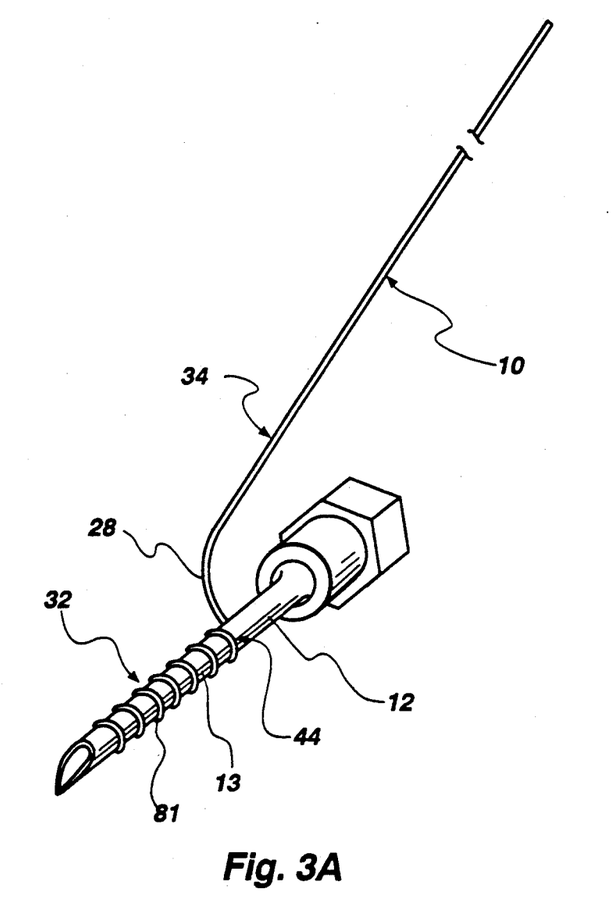
FIG. 3A is a perspective view of an alternative embodiment of the guide wire.

Nitinol, or a similar material having properties of "memory," may also be used to provide a guide wire 10. As shown by FIG. 3A, the guide wire 10 has a first portion 32 which is configured into a plurality of coils 81 or loops wrapped or coiled about the elongated portion 13 of the trocar 12. The second portion 34 is a non-coiled but flexible wire. The second portion 34 may also be made of nitinol or alternately some other suitable material. For a guide wire 10 of the type shown in FIG. 3A, the first portion 32 is shaped about the trocar 12. The trocar 12 is then inserted through the patient's tissue into the body. After the trocar 12 is placed in the patient's body, it is preferably removed through access 44. After placement in the body, the first portion 32 of the guidewire, due to the "memory" properties, will return to a linear configuration.

Figures 4, 5:
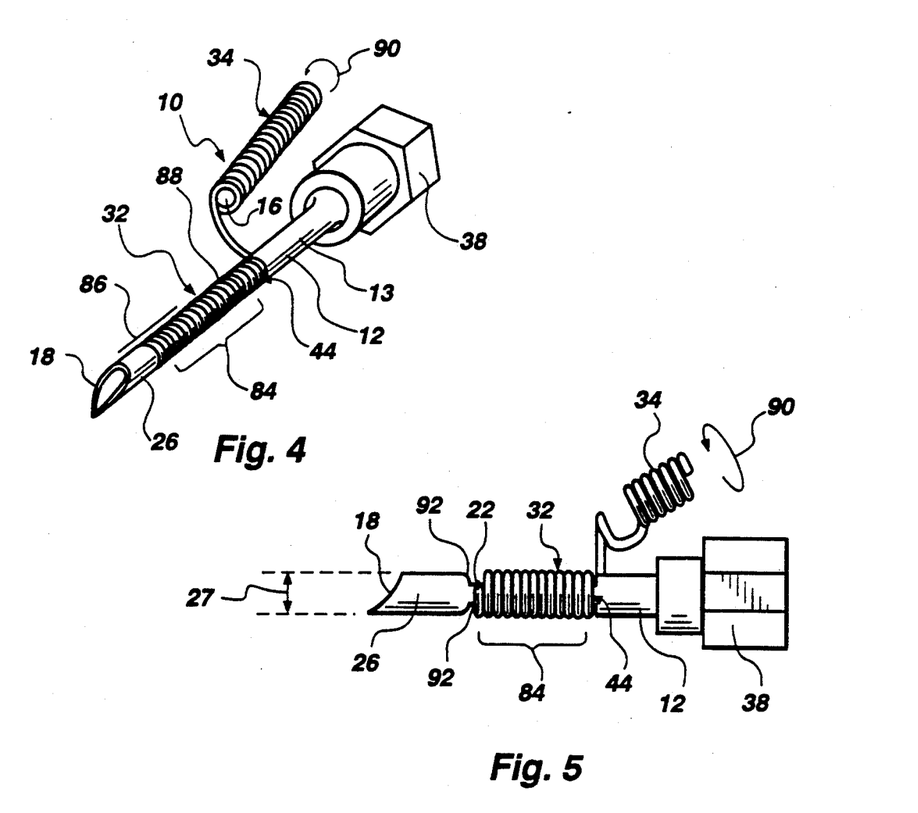
FIG. 4 is a perspective view of an alternative embodiment of a guide wire positioned about a trocar.
FIG. 5 is an enlarged side view of the embodiment shown in FIG. 4.

To reduce the resistance encountered between the tissue and the guide wire 10 when the guide wire 10 and trocar 12 are inserted into the patient's body, the trocar 12 may, as illustrated by FIGS. 4 and 5, be formed with a recessed section 84 between the tip 18 and the hub 38 of the trocar 12. The first portion 32 of the guide wire 10 is positioned about the trocar 12 and within the recessed section 84 to present a relatively smooth and continuous surface 86 between the exterior surface 26 of the trocar 12 and the exterior surface 88 of the first portion 32 of the guide wire 10. In this embodiment, when the trocar 12 is to be removed from the first portion 32 of the guide wire 10, the second portion 34 of the guide wire may be manually rotated in direction 90, opposite the direction of coiling to cause the lumen 16 of the first portion 32 of the guide wire 10 to increase in diameter so that the trocar 12 may be removed via access 44. To facilitate removal of the trocar 12 from the first portion 32, the proximal edge 92 of the tip 18 of the trocar 12 may be arcuately shaped to facilitate movement of tip 18 of the trocar 12 through the tip 22 of the guide wire 10.

In many medical procedures where a trocar 12 and guide wire 10 are being introduced into a patient's body, it may be necessary or desirable to enlarge the opening made by the trocar 12 in the tissue by enlargement or dilation means to allow insertion of a cannula or other instrument including structure which has a greater diameter 27 than the trocar 12. Therefore, it may be desirable to provide enlargement structure in association with the guide wire 10 for increasing the diameter of the opening into the patient's body. To that end, the guide wire 10 may have, or be associated with, various enlargement structures which have increasing cross sectional dimension.

Figures 6, 7:
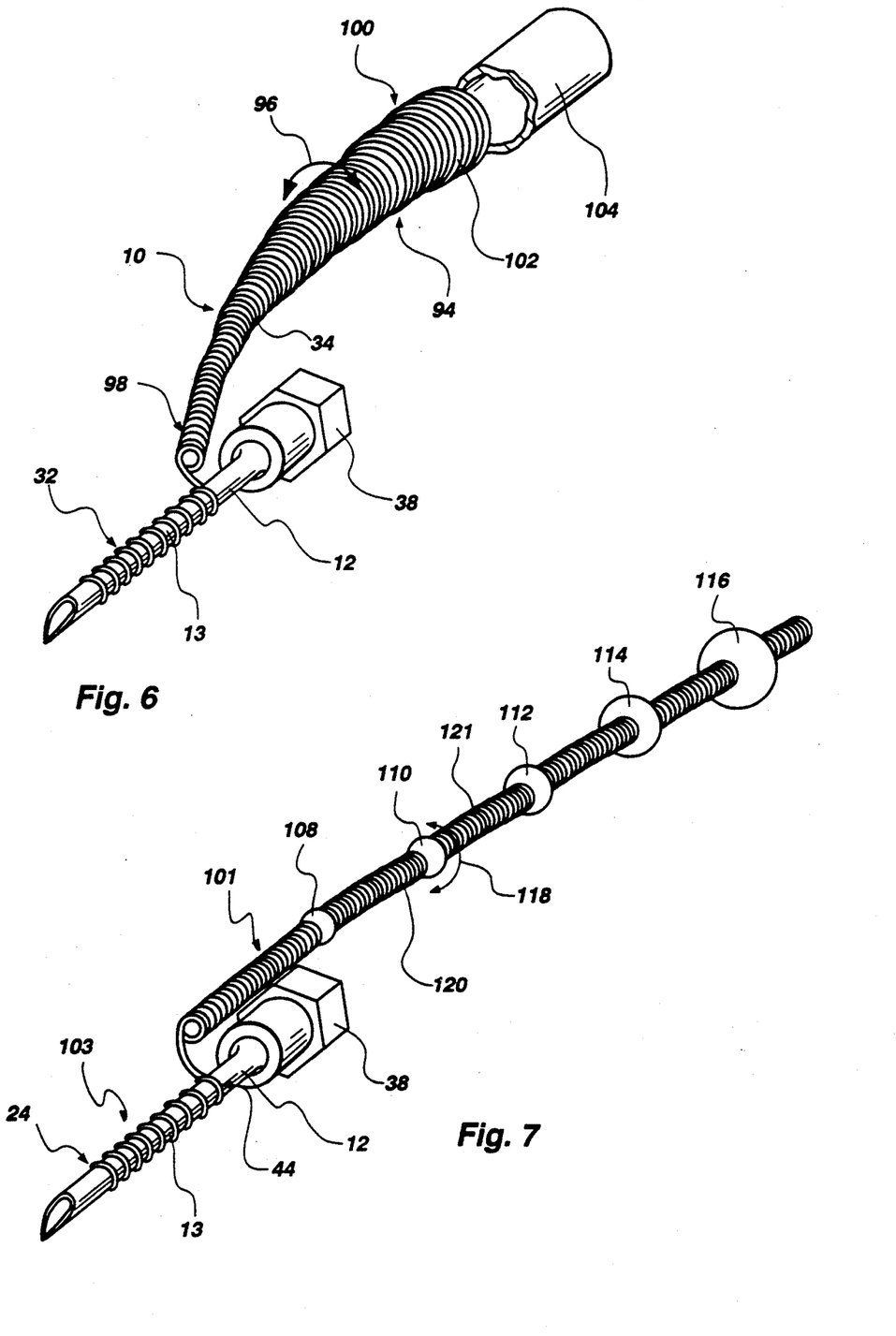
FIG. 6 is a perspective view of a guide wire having enlarging means associated therewith.
FIG. 7 is a perspective view of a guide wire having alternative means of enlargement associated therewith.

FIG. 6 illustrates a guide wire 10 having enlargement structure 94 where the circumference 96 of the guide wire 10 gradually increases from a smaller circumference proximate the distal end 98 of the second portion 34 to a larger circumference proximate the proximal end 100 of the guide wire 10. In the embodiment illustrated by FIG. 6, the second portion 34 of the guide wire 10 extending away from the trocar 12 may be relatively less elastic than the first portion 32. The enlargement structure 94 may be continuous coils 102 or loops of the guide wire 10, or the enlargement structure 94 may be a hollow channel 104 of solid material joined with the coils 102 and may be similar to a standard dilator used in surgical procedures and well-known to those in the art. Even though a circular cross section in second portion 34 is shown, other cross sectional shapes may be employed as desired.

In an alternative embodiment, as illustrated in FIG. 7, the guide wire 101 may have associated therewith a plurality of enlargement or dilating structures, such as beads 108, 110, 112, 114, and 116 in the second portion 120. The beads 108, 110, 112, 114 and 116 increase the diameter of the opening in the body made by the trocar 12 and first portion 103 of guide wire 101. That is, after the trocar 12 and first portion 103 of the guide wire 101 are inserted into the patient and the trocar 12 is removed through access 44, the guide wire 101 is advanced into the patient. The diameter of the opening (not shown) in the patient formed by insertion of the trocar 12 and guide wire 101 is increased as the first enlargement means 108 passes through the opening. The circumference 118 of each enlargement means associated with the guide wire 101 increases in relation to its distance from the distal end 24 of the guide wire 101. That is, the farther an enlargement means is located from the distal end 24 of the guide wire 101 the greater is its circumference 118. Therefore, as the guide wire 101 is advanced further into the patient, the passage of each successive enlargement structure or bead 108, 110, 112, 114 and 116 increases the diameter of the opening (not shown) in the patient. Even though the enlargement structure 108, 110, 112, 114 and 116 is shown to be spherical in shape, other geometric shapes may be used as desired. That is, serial enlargement structure illustrated by FIG. 7 may take any form which provides increasing cross section of the guide wire 101 to dilate the opening formed in the tissue of the patient. Alternatively, the enlargement structure may be formed by intermittent segments or stepped sections of coils which are enlarged relative to the coils 121 positioned directly on either side thereof.

Figure 8:
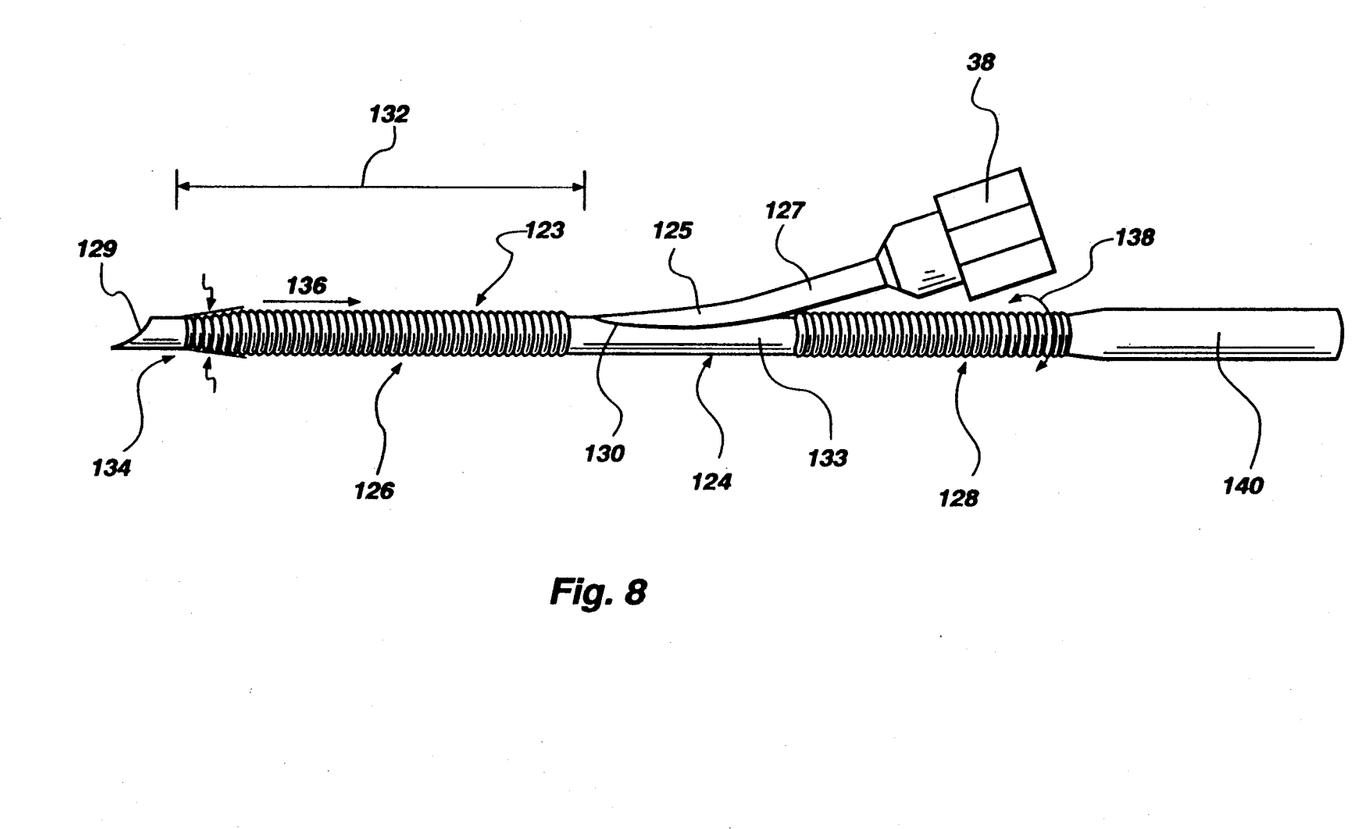
FIG. 8 is a side view of an alternative embodiment of a guide wire of the invention with a trocar inserted therethrough.

In FIG. 8, the guide wire 123 may be formed with a hollow tube 124 defining an intermediate section, positioned intermediate a distal portion 126 and a proximal portion 128. The hollow tube 124 has a wall 133 defining a central bore (not shown) and an opening 130 formed in the wall 129 thereof which is sized and adapted to receive needle-like means, such as the elongated portion 125 of a trocar 127, therethrough. The distal portion 126 of the guide wire 123 has a lumen (not shown) of sufficient internal diameter to receive needle-like means slidably positioned therethrough. The distal portion 126 of the guide wire 123 is sized in length 132 so that the tip 129 of the trocar 127 extends past the distal end 134 of the guide wire 123 to allow piercing of the patient's body. The proximal portion 128 of the guide wire 123 is sized in length to extend from proximate the intermediate tube 124 to exterior the patient's body.

In use, the tip 129 of the trocar 127 is positioned at the desired point of entry of a patient's body (not shown). The tip 129 is urged into the patient to penetrate the tissue. The tip 129 and distal portion 126 of the guide wire 123 are advanced into the patient's body. Thereafter, the trocar 127 is withdrawn in direction 136 from the distal portion 126 through the opening 130 in the hollow tube 124. The guide wire 123 may then be advanced to the interior of the patient's body a desired distance.

The proximal portion 128 of the guide wire 123 shown in FIG. 8 may be uniform in circumference 138 along the length thereof, as illustrated. It may have a dilator 140 slidably disposed about the guide wire 123 for advancement into the opening formed in the patient's body. Alternatively, the proximal portion 128 of the guide wire 123 may have enlargement structure associated therewith as illustrated in FIGS. 6 and 7.

Figure 9:
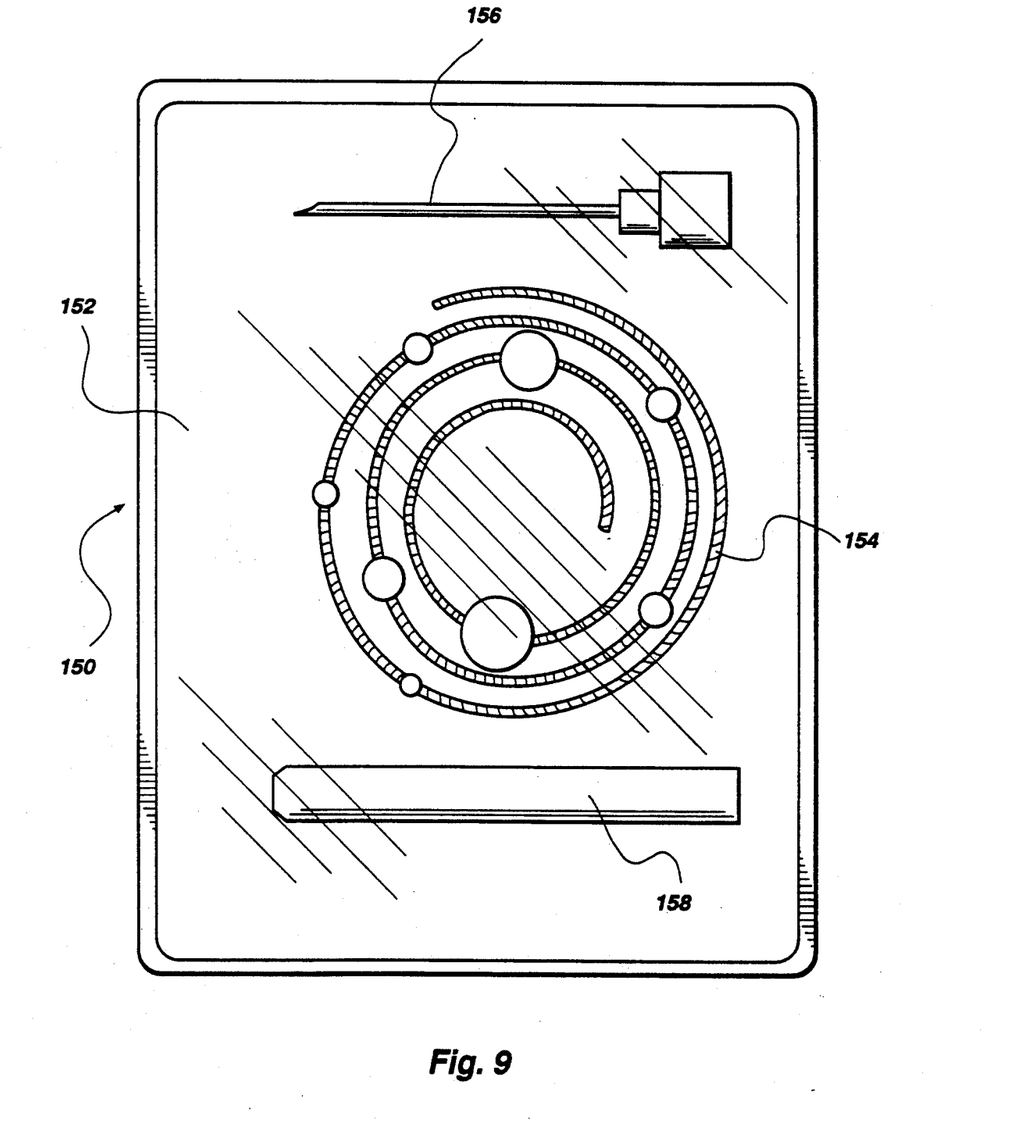
FIG. 9 is a plan view of a kit including the structure of the invention.

FIG. 9 illustrates a kit 150 usable by medical personnel for effecting the placement of a guide wire 154 into a patient. The kit 150 includes a package 152 sized to receive a guide wire 154 and a trocar 156 for use with the guide wire 154. A cannula 158 may also be included for use with the guide wire 154 in performing a cannulation procedure. The package 152 is overwrapped in a manner to maintain the sterile state of the contents therein until use.

The present invention is directed to procedures requiring the insertion of medical apparatus into the body of a patient, and particularly to facilitating the insertion of such apparatus with the aid of a guide wire. The present invention may be used in a variety of applications where insertion of medical apparatus is required. The structure of the invention may be modified to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the claims which follow.

What is claimed is:

1. A method of inserting a guide wire into a patient comprising:

providing structure for insertion into the tissue of a patient comprising needle-like structure having an elongated portion, said elongated portion having an exterior surface, a proximal end and a distal end defining piercing means for inserting said needle-like structure into the tissue of a patient, and a guide wire having a body, said body having a distal end, a proximal end, and a lumen sized and shaped for positioning slidably and snugly about said exterior surface of said elongated portion of said needle-like structure, said body being sized in length to extend from interior a patient to exterior said patient;

positioning said piercing means proximate said tissue of said patient for insertion therethrough;

inserting said elongated portion and said distal end of said body into said tissue of said patient to form an opening therethrough;

removing said elongated portion from said distal end of said body; and urging said body of said guide wire into said opening a selected distance.

2. The method according to claim 1 wherein said structure for insertion into the tissue of a patient further includes dilation means associated with said body of said guide wire, and further comprising the step of inserting said dilation means through said opening to enlarge said opening.

3. Structure for insertion into the tissue of a patient comprising:

needle-like structure having an elongated portion, said elongated portion having an exterior surface, a proximal end and a distal end defining piercing means for inserting said needle-like structure into the tissue of a patient;

a guide wire having a body, said body having a distal end, a proximal end, and a lumen sized and shaped for positioning slidably and snugly about said exterior surface of said elongated portion of said needle-like structure, and a transition section positioned between a first portion and a second portion of said body to facilitate positioning of said first portion away from said second portion, said body being sized in length to extend from interior a patient to exterior said patient; and enlargement means associated with said body for dilating an opening made through said tissue by said piercing means.

4. The structure of claim 3 wherein said distal end of said body has an outer surface configured to taper toward said piercing means of said elongated portion of said needle-like structure.

5. The structure of claim 4 wherein the cross section of said body gradually increases to provide said enlargement means for dilating said opening, said increase in cross section occurring in a direction away from said transition section and along said length of said body toward said proximal end.

6. The structure of claim 5 wherein said body of said guide wire is a continuous length of material formed into a plurality of adjacent coils.

7. The structure of claim 6 wherein the cross section of said body comprising said coils increases to provide said enlargement means.

8. The structure of claim 7 further comprising a hollow channel of solid material connected to said coils at said proximate end, said hollow channel being shaped to provide increasing cross section in a direction away from said transition section and along said length of said body toward said proximal end.

9. The structure of claim 4 wherein said enlargement means is a plurality of dilating structures positioned along said length of said proximal end of said body, said dilating structures each having a cross section, the cross section of each said dilating structures being larger than the next preceding dilating structure positioned proximate said transition section.

10. The structure of claim 4 wherein said enlargement means is a hollow cylindrical structure sized to receive said body of said guide wire therethrough, said hollow cylindrical structure having a gradually increasing cross section.

11. Structure for insertion into the tissue of a patient comprising:

needle-like structure having an elongated portion, said elongated portion having an exterior surface, a proximal end and a distal end defining piercing means for inserting said needle-like structure into the tissue of a patient;

a guide wire having a body, said body having a distal end, a proximal end, and a lumen sized and shaped for positioning slidably and snugly about said exterior surface of said elongated portion of said needle-like structure, said body being sized in length to extend from interior a patient to exterior said patient; and a tube positioned proximate said distal end of said body, said tube having an opening therein and a bore sized and shaped to receive said elongated portion of said needle-like structure therethrough, said piercing means extending beyond said distal end of said body when said needle-like structure is inserted through said tube.

12. The structure of claim 11 wherein said distal end of said body has an outer surface configured to taper toward said exterior surface of said elongated portion of said needle-like structure.

13. The structure of claim 12 wherein said proximal end of said body has enlargement means associated therewith for dilating an opening made through said tissue by said piercing means.

14. Structure for insertion into the tissue of a patient comprising:

needle-like structure having an elongated portion, said elongated portion having an exterior surface, a proximal end and a distal end defining piercing means for inserting said needle-like structure into the tissue of a patient;

a guide wire having a body, said body having a distal end, a proximal end, and a lumen sized and shaped for positioning slidably and snugly about said exterior surface of said elongated portion of said needle-like structure, said body being sized in length to extend from interior a patient to exterior said patient; and a transition section formed between a first portion and a second portion of said body, said first portion comprising a continuous length of material formed into a plurality of coils and said second portion being uncoiled, said second portion being positioned proximate said proximal end.

15. The structure of claim 14 wherein said distal end of said body has an outer surface configured to taper toward said piercing means of said elongated portion of said needle-like structure.

16. The structure of claim 15 further comprising enlargement means associated with said body for dilating an opening made through said tissue by said piercing means.

17. Structure for insertion into the tissue of a patient comprising:

needle-like structure having an elongated portion, said elongated portion having an exterior surface, a proximal end and a distal end defining piercing means for inserting said needle-like structure into the tissue of a patient;

a guide wire having a body, said body having a distal end, a proximal end, and a lumen sized and shaped for positioning slidably and snugly about said exterior surface of said elongated portion of said needle-like structure, said distal end being configured to have a smaller cross section than the cross section of said elongated portion and being fixedly adaptable to enlarge in cross section to be positionable about said elongated portion; and a transition section between a first portion and a second portion of said body, said second portion of said body being positionable away from said first portion.

18. The structure of claim 17 wherein said elongated portion of said needle-like structure further includes a recessed portion extending from proximate said distal end of said elongated portion to proximate said proximal end of said elongated portion, said recessed portion being sized to receive a portion of said distal end of said guide wire.

19. The structure of claim 18 wherein said distal end of said needle-like structure further comprises an edge contiguous with said recessed portion, said edge being arcuately formed between said recessed portion and said piercing means.

* * * * *

UNITED STATES PATENT AND TRADEMARK OFFICE
CERTIFICATE OF CORRECTION

PATENT NO.   : 5,209,735

DATED        : 5/11/93

INVENTOR(S)  : Harrison M. Lazarus

It is certified that error appears in the above-indentified patent and that said Letters Patent is hereby corrected as shown below:

In Column 1, line 60, change "Wire" to --wire--;

In Column 5, line 2, change "6" to --26--;

In Column 5, line 16, change "8" to --18--;

In Column 7, line 36, change "129" to --133--;

In Column 9, line 24, change "proximate" to --proximal--;

In Column 9, line 33, change "structures" to --structure--;

In Column 10, line 46, change "fixedly" to --flexibly--.

Signed and Sealed this

Twenty-fourth Day of May, 1994

Attest:

BRUCE LEHMAN

Attesting Officer    Commissioner of Patents and Trademarks